United States Patent [19]

Lang

[11] 4,283,556
[45] Aug. 11, 1981

[54] PROCESS FOR THE MANUFACTURE OF SUBSTANTIALLY PURE 3-AMINO-4-ALKOXY-ACYLANILIDES FROM 2,4-DINITROCHLOROBENZENE

[75] Inventor: Philip C. Lang, Dover Township, Ocean County, N.J.

[73] Assignee: Toms River Chemical Corporation, Toms River, N.J.

[21] Appl. No.: 119,245

[22] Filed: Feb. 7, 1980

Related U.S. Application Data

[63] Continuation of Ser. No. 941,533, Sep. 11, 1978, abandoned.

[51] Int. Cl.$^3$ .......................................... C07C 102/00
[52] U.S. Cl. .............................. 564/144; 260/465 D; 564/133; 564/50; 564/86; 564/156; 564/166; 564/170; 564/182; 564/184; 560/29
[58] Field of Search .......... 260/562 R, 556 A, 465 D; 562/29; 564/50, 144, 133, 86

[56] References Cited

U.S. PATENT DOCUMENTS

| | | | |
|---|---|---|---|
| 3,919,314 | 11/1975 | Marriott | 260/562 T |
| 4,005,143 | 1/1977 | Bohm et al. | 260/580 |
| 4,009,205 | 2/1977 | Kimura et al. | 260/556 A |
| 4,013,621 | 3/1977 | Knell | 260/556 A |
| 4,026,944 | 5/1977 | Bohm et al. | 260/580 |
| 4,079,079 | 3/1978 | Gait | 260/562 R |

FOREIGN PATENT DOCUMENTS

1543625 of 0000 Fed. Rep. of Germany .
1324303 7/1973 United Kingdom .

OTHER PUBLICATIONS

Beckwith, The Chemistry of Amides, 1970, Interscience Publishers, N.Y., N.Y., pp. 77–81.
Wagner et al., Synthetic Organic Chemistry, John Wiley & Sons, N.Y., N.Y., 1975, p. 654.

*Primary Examiner*—Arthur P. Demers
*Attorney, Agent, or Firm*—Edward McC. Roberts

[57] ABSTRACT

A process for the manufacture of a substantially isomerically pure acylanilide of the structure

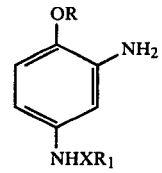

where R is hydrogen, lower alkyl, hydroxy-lower alkyl or lower alkoxy-lower alkyl;
$R_1$ is lower alkyl, phenyl, lower alkylphenyl, lower alkoxy, lower alkoxyphenyl, chlorophenyl, nitrophenyl, dichlorophenyl, chloro-lower alkyl, cyano-lower alkyl, lower alkyl amino, sulfamoylphenyl, carbamoylphenyl or lower alkoxy-lower alkyl; and
X is —CO— or —SO$_2$—;

comprising the step of treating an alcohol solution of a diamino compound of the structure

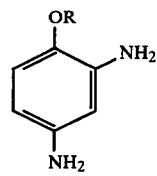

with an acylating agent, to give an alcohol solution of the acylanilide, wherein substantially equivalent amounts of the acylating agent and the diamino compound are used and wherein the treatment is carried out by the slow, drop-wise addition of the acylating agent at a temperature in the range of about 0° to 5° C. The process is particularly advantageous when the alcohol solution of the diamino compound is produced by reduction of a suspension of the corresponding dinitro compound in the alcohol.

12 Claims, No Drawings

PROCESS FOR THE MANUFACTURE OF SUBSTANTIALLY PURE 3-AMINO-4-ALKOXY-ACYLANILIDES FROM 2,4-DINITROCHLOROBENZENE

This is a continuation of application Ser. No. 941,533 filed on Sept. 11, 1978 now abandoned.

BACKGROUND OF THE DISCLOSURE AND BRIEF DESCRIPTION OF THE INVENTION

In the manufacture of many commercial or potentially commercial azo dyes, a key intermediate is an anilide coupler intermediate of the structure set out as formula I

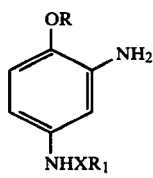

where R is hydrogen, lower alkyl, hydroxy-lower alkyl or lower alkoxy-lower alkyl $R_1$ is lower alkyl, phenyl, lower alkylphenyl, lower alkoxy, lower alkoxyphenyl, chlorophenyl, nitrophenyl, dichlorophenyl, chloro-lower alkyl, cyano-lower alkyl, lower alkylamino sulfamoylphenyl, carbamoylphenyl or lower alkoxy-lower alkyl; and X is —CO— or —SO$_2$—. (Throughout this specification, R, $R_1$ and X have the meanings here designated, unless it is specifically stated otherwise.)

Such commercial azo dyes are found, for example, in U.S. Pat. Nos. 916,323; 3,232,693; 3,268,507; 3,325,471; 3,520,871; 3,522,235; 3,533,722 and 3,740,189.

In commercial practice, anilides of the structure of formula I have commonly been made according to the following reaction sequence:

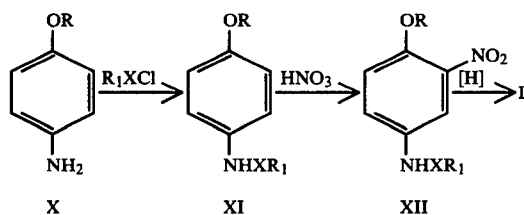

This rather expensive manufacturing procedure results in the desired product I without contamination with the isomeric compound XIII or the diacyl compound XIV.

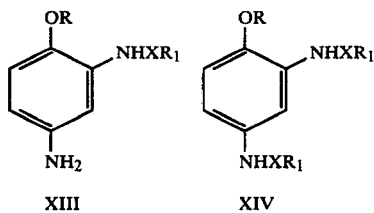

According to Example 6 of U.S. Pat. No. 3,919,314, which issued Nov. 11, 1975 on application of Richard John Merriott, the direct acylation of 2,4-diaminoanisole with acetic anhydride in aqueous solution in the presence of hydrochloric acid gives a mixture of compounds I and XIII where R is methyl and —$XR_1$ is —$COCH_3$. U.S. Pat. No. 4,079,079, which issued Mar. 14, 1978 on application of Richard James Gait also teaches the production of a mixture of isomers I and XIII by acetylation of 2,4-diaminoanisole dihydrochloride in aqueous solution at a maintained pH of 1.5-3.5.

Other aqueous processes of acylation have been taught to yield the single desired isomer compound I where R is —$CH_3$ and —$XR_1$ is —$COCH_3$, but at lower yield. German 1,543,625, Example 1, teaches the acylation of freshly-distilled 2,4-diaminoanisole with acetic anhydride in water solution, without the addition of hydrochloric acid, to give 3-amino-4-methoxyacetanilide in 75% yield before recrystallization. Publication, Board of Federal Intelligence Agency, P.B. 74 051, p. 33 teaches a similar conversion of 2,4-diaminoanisole to 2-amino-4-acetamidoanisole, in aqueous solution, with acetic anhydride, in the presence of magnesia at 65% yield.

It is thus quite surprising that substitution of an alcohol for the water of the P.B. 74 051 procedure gives a markedly improved yield of 90-92% while still maintaining the selectivity needed to give compound I exclusively. The process here taught and claimed further differs from the P.B. 74 051 procedure in not using an excess of acylating agent and in adding the acylating agent to the 2,4-diaminoanisole (or equivalent 2,4-diaminophenol or other ether thereof) at a lower temperature.

British Pat. No. 1,324,303 teaches the acetylation of 2,4-diamino-1-(beta-phenoxyethoxy) benzene in alcoholic solution, in the presence of magnesia. However, British Pat. No. 1,324,303 uses an excess of acylating agent, added at room temperature, rather than at 0° to 5° C., and without the slow or dropwise addition of the acylating agent. Analysis of the acetylated product is not given in the British patent. The British patent does not teach the acetylation of any simple lower alkyl ethers of 2,4-diaminophenol. Acetylation of 2,4-diaminoanisole according to the procedure of the British patent, has been found to give a 77-80% yield of compound I, contaminated with 20-22% of compound XIV and 0.4% of compound XIII.

It is further to be noted that all of the above-described acylation procedures, except that of British Pat. No. 1,324,303, require freshly-distilled 2,4-diaminoanisole or its equivalent as starting material. Inasmuch as 2,4-diaminoanisole is carcinogenic, it is advantageous to manufacture the desired coupler intermediate, 3-amino-4-methoxyacetanilide, or its equivalent, without isolation of the diamino starting material.

DETAILED DESCRIPTION OF THE INVENTION

By the process of this invention, the desired coupling intermediate compound I is obtained, substantially pure, in high yield from 2,4-dinitrochlorobenzene, according to the following reaction scheme:

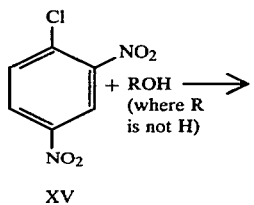

XV

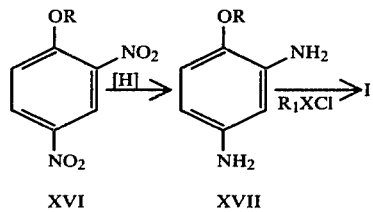

XVI    XVII

The yield of I by this procedure is 80–85% of theory, based on starting material XV. Typically the acylation product containing isomerically pure product I, obtained by this procedure, analyzes as follows: 90% I, 3.5% XIV, 0.5% XVII, 0.75% ash, and 4.7% water, with no detectable amount of the isomeric product XIII. The yield and analysis here reported is obtained on the final product I, produced by the three-step synthesis set out above, without isolation of the intermediates XVI and XVII. As can be appreciated, an overall yield of 80–85% in a three-step synthesis, requires an average yield of about 95% for each of the three steps. As to purity of the organics in the product, subtracting out ash and water, one finds the product to be 95.7% I, 3.7% XIV and 0.5% XVII. For the manufacture of azo-dyes, this product is substantially pure and can be used with no practical distinction over the product obtained by the art process, X→XI→XII→I.

It is critical to the success of this process that the $R_1X$-acylating agent, used in the last step of this process be used in an amount (by weight) that is substantially equivalent to the diamino compound XVII. It is further critical that the $R_1X$-acylating agent be added slowly at a substantially constant rate, for instance, dropwise over a period of about 1 to about 3 hours, preferably about 1.5 to about 2 hours, at a temperature in the range of about $-5°$ to about 15° C., preferably about 0° to about 5° C., such that the acylation is substantially complete before the temperature is raised above the selected reaction temperature. The lower limit of the time range for the addition of the acylating agent is critical, to allow the acylation to proceed without any temporary and local build-up of excess acylating agent in the reaction solution. The upper limit is not critical and can be extended at will. The lower temperature range is selected so as to give a reasonable reaction rate. The upper temperature range is governed by the discovery that the amount of di-acylation, versus the desired mono-acylation, increases with the reaction temperature. Below about 5° C. there is very little or no di-acylation. Above about 15° C. the product will be contaminated with substantial amounts of di-acylated product and, in view of the strict stoichiometric addition of acylating agent, corresponding amounts of non-acylated diamine.

Any of the commonly used acylating agents of the art are eligible for use herein. The chosen acylating agents are those that will attach an $R_1X$-group to an amine, namely the $R_1X$-acylating agents, such as acetyl-acylating agents or methanesulfonyl-acylating agents. By $R_1X$-acylating agent is thus meant an acylating agent that converts an amine, such as aniline, to an amide, such as an anilide, thus: $C_6H_5NH_2 \rightarrow C_6H_5NHXR_1$. Exemplary of eligible $R_1X$-acylating agents are acid halides, particularly acid chlorides and acid bromides such as acetyl chloride, benzoyl chloride, benzenesulfonyl chloride and the like, lower alkyl isocyanates such as ethyl isocyanate and the like and acid anhydrides, such as acetic anhydride, propionic anhydride and the like.

It is particularly advantageous to carry out the described inventive process without isolation of the intermediates XVI and XVII. Both intermediates XVI and XVII are formed and obtained in alcohol solution by this procedure, and are advantageously used without isolation therefrom.

As a special non-preferred example of this process, where R is H, 2,4-dinitrophenol (XVI) is reduced to 2,4-diaminophenol (XVII) and acylated to give I where R is H. The latter compound, if desired, may be etherified, particularly with a di-(lower alkyl)sulfate, to give I where R is lower alkyl.

As can be appreciated from the above descriptions, the reactions of this process are advantageously carried out in an alcoholic medium. When R of compounds XVI, XVII and I is other than hydrogen, the alcohol used in converting 2,4-dinitrochlorobenzene to compound XVI is, of necessity, of structure ROH. For the conversion of XVI to XVII to I, where R is other than H, the alcohol ROH may be used as the medium, or any lower alcohol, particularly methanol or ethanol. When R of compounds XVI, XVII and I is hydrogen, the synthesis is started with 2,4-dinitrophenol (XVI where R is H) and the chosen alcohol for the reaction medium may be any alcohol of structure ROH, where R is not hydrogen, particularly methanol or ethanol.

The process of this invention is further illustrated by the following specific examples.

EXAMPLE 1

Conversion of 2,4-Dinitrochlorobenzene to 3-Amino-4-Methoxyacetanilide (Step 1) Into a 2 liter flask equipped with stirrer, reflux condenser and thermometer was charged 632 g. methanol and 213 g. melted 2,4-dinitrochlorobenzene (mp. 47° C.). The mass was stirred to give a solution. To this stirred solution was added 86 g. of 50% aqueous sodium hydroxide solution (or 42 g. of sodium hydroxide flake) at a rate to heat the reaction solution to gentle reflux. After all the sodium hydroxide had been added, the reaction solution was heated at reflux for one hour. The heat was removed and the reaction mass was allowed to cool.

(Step 2) The entire reaction mass now containing 2,4-dinitroanisole was charged into a 2 liter Parr autoclave bomb, model 4522, purged with nitrogen, and treated by addition of 4.0 g. of 5% palladium on carbon. The bomb was purged with hydrogen and pressurized to about 60 psig with rapid agitation. The temperature rose adiabatically to 60° C., after which cooling was required to maintain 60° C. until hydrogen uptake ceased and the reduction was complete. The bomb was then cooled, vented and purged with nitrogen, and the catalyst filtered off. The washed catalyst may be used 5–6 times. The resulting 2,4-diaminoanisole/methanol solution is assayed for 2,4-diaminoanisole by perchlorate titration. The yield of 2,4-diaminoanisole, based on the 2,4-dinitroanisole, was essentially quantitative. The perchlorate assay was run on an accurately weighed 2 to 3 g. aliquot of the reaction solution, diluted with 70 and 80 ml. of acetonitrile. The sample was titrated potentiometrically with a glass/calomel electrode, using 0.2 N perchloric acid.

(Step 3) The above 2,4-diaminoanisole/methanol solution was charged into a 2-liter flask equipped with stirrer, dropping funnel, thermometer and gas inlet/exit tubes. The reaction flask was purged with nitrogen and cooled to 0° to 5° C. To the reaction flask was added 22 g. magnesium oxide, followed by exactly one equivalent weight of acetic anhydride, based on the analysis of the 2,4-diaminoanisole, added dropwise over 1¾ to 2 hours at a uniform rate. For each mole of 2,4-diaminoanisole, 102 g. acetic anhydride was used. The reaction mass was maintained at 0° to 5° C. during the addition of the acetic anhydride. The reaction mass was then heated to distill off approximately 700 ml. methanol. 300 ml. water was added and distillation was continued until the pot temperature reached 98° C. The reaction mass was cooled to room temperature and adjusted in volume to 550 ml. by addition of water. After further cooling to 0° to 5° C., the reaction product was obtained by filtration. The product on the filter was washed twice with two 50 ml. portions of ice water and and air dried to give 167 g. of substantially pure product, which analyzed as 151 g. of 3-amino-4-methoxyacetanilide, 5.9 g of 3-acetamido-4-methoxyacetanilide, 0.8 g. of 2,4-diaminoanisole, 0.8 g. of ash, and 7.9 g. of water, with no detectable 5-amino-2-methoxyacetanilide. The 151 g. yield of 3-amino-4-methoxyacetanilide represents 80% of theory, based on the 2,4-dinitrochlorobenzene starting material. In repeated runs, the yield of 3-amino-4-methoxyacetanilide (excluding any ash, water, 2,4-diaminoanisole and 3-acetamido-4-methoxyacetanilide, as above) was 80–85% of theory based on 2,4-dinitrochlorobenzene, and 90–92% of theory based on 2,4-diaminoanisole.

The percents of mono- and di-acetylated material were determined by liquid chromatography, using a Waters Associates Model ALC 202 chromatographic apparatus with a Microbondapak C-18 column of 0.25 inch o.d.×1 foot, with 3:1 distilled water-methanol as eluant and an internal standard of pure material.

The percent of non-acetylated diamino-compound was determined by thin layer chromatography, using silica gel on aluminum sheets with eluant of 7:1:2 xylene:acetone:3A ethanol plus 10% ammonium hydroxide, and with spot development by means of a spray of 1% p-dimethylaminobenzaldehyde in 1:1 methanol:2 N hydrochloric acid.

EXAMPLE 2

Alternate Reduction of 2,4-Dinitroanisole

The reaction mass from the first step of Example 1, containing 2,4-dinitroanisole was treated by the addition of 800 g. of ice. The resulting solid 2,4-dinitroanisole was isolated by filtration and washed with 1 to 2 liters of cold water. The wet presscake was added slowly (exothermic), over a period of 1 hour, to a mixture of 1200 g. water, 400 g. iron powder and 60 g. acetic acid, at 85°–90° C., under a nitrogen atmosphere. The reaction mass was held for about 1 hour at 90°–95° C., cooled to about 5° C., and treated with 80 g. of 50% aqueous sodium hydroxide and an exact equivalent of acetic anhydride (about 90 g). The reaction mass was analyzed for 2,4-diaminoanisole, by perchlorate titration (as described in Example 1) prior to the alkali addition. The acetic anhydride was added dropwise, over a period of about 2 hours, while the temperature of the reaction mass was maintained at about 0° to 5° C. Following the addition of the acetic anhydride, the pH was adjusted to 6.8–7.0. The reaction product was treated with 20 g. of activated charcoal and 10 g. of diatomaceous earth at 95° C. and filtered to clarify. The filter residue was washed three times with 100 ml. of hot water. The combined filtrate and washings was treated with salt (to 10%), cooled to 0° to 5° C., and filtered to give substantially pure crystalline product, which assayed at 129 g. of 3-amino-4-methoxyacetanilide, 68% of theory based on the 2,4-dinitrochlorobenzene starting material.

EXAMPLE 3

3-Amino-4-Ethoxyacetanilide

According to the procedure of Example 1, substituting 632 g. of ethanol for the methanol used therein, 2,4-dinitrochlorobenzene was converted to 3-amino-4-ethoxyacetanilide, in 80% yield.

EXAMPLE 4

3-Amino-4-Methoxypropionanilide

According to the procedure of Example 1, substituting 130 g. of propionic anhydride for the acetic anhydride used therein, 2,4-dinitrochlorobenzene was converted to 3-amino-4-methoxypropionanilide, in 80% yield.

EXAMPLE 5

3-Amino-4-Methoxybenzanilide

According to the procedure of Example 1, substituting 135.5 g. of benzoyl chloride for the acetic anhydride used therein, 2,4-dinitrochlorobenzene was converted to 3-amino-4-methoxybenzanilide, in 79% yield.

EXAMPLE 6

3-Amino-4-Methoxybenzenesulfonanilide

According to the procedure of Example 1, substituting 176.5 g. of benzenesulfonyl chloride for the acetic anhydride used therein, 2,4-dinitrochlorobenzene was converted to 3-amino-4-methoxybenzenesulfonanilide, in 77% yield.

EXAMPLE 7

3-Amino-4-Propoxyacetanilide

According to the procedure of Example 1, substituting 632 g. n-propanol for the 632 g. methanol used therein, 2,4-dinitrochlorobenzene was converted to 3-amino-4-propoxyacetanilide, in 77% yield.

EXAMPLE 8

3-Amino-4-Hydroxyacetanilide

According to the procedure of Example 2 and Step 3 of Example 1, substituting 184 g. of 2,4-dinitrophenol for the 2,4-dinitroanisole used therein, a methanol solution of isomerically pure 3-amino-4-hydroxyacetanilide was produced in good yield. For use as a coupler intermediate, the 3-amino-4-hydroxyacetanilide of this Example may be etherified by treatment of the methanol solution thereof with sodium hydroxide to make the sodium salt of the phenol, followed by dimethylsulfate at 30° to 35° C.

EXAMPLE 9

3-Amino-4-Ethoxyacetanilide by Solvent Bechamp Reduction

Into a 2-liter resin kettle, equipped with stirrer, reflux condenser and thermometer, was charged 632 g. ethanol. To the ethanol was added carefully, below 50° C., in 15–20 minutes, 42.0 g. sodium hydroxide. To this was added, in 15 to 20 minutes, 213 g. 2,4-dinitrochlorobenzene, with the temperature maintained below 50° C. The resulting mixture was heated to reflux and held at reflux for 3 hours to give an ethanol solution of 2,4-dinitrophenetole. After cooling to room temperature, the ethanolic reaction solution was treated with 340 g. iron powder and 200 ml. water, exhibiting a mild exotherm. A solution of 12 ml. hydrochloric acid, 12 ml. glacial acetic acid and 100 ml. water was added dropwise over 1 hour at a rate to maintain 62°–75° C. This reaction mass was refluxed under a nitrogen atmosphere for 3 hours, then cooled to 0° to 5° C., and assayed for 2,4-diaminophenetole by perchlorate titration. To the cooled reaction mass was added 80 g. sodium hydroxide (50% aqueous solution), and then an exact equivalent amount of acetic anhydride, about 90–94 g. acetic anhydride, depending on the perchlorate assay. The temperature was maintained at 0° to 5° C. during this addition. The acetic anhydride was added dropwise over a period of about 2.5 hours. Following the addition of the acetic anhydride, the pH was adjusted to 6.8–7.0. The reaction product was treated with 20 g. of activated charcoal and 10 g. of diatomaceous earth at 80° C. and filtered to clarify. The filter residue was washed three times with 50 ml. of hot 1:1 ethanol-water. The combined filtrate and washings was heated to distill off ethanol, until the pot temperature reached 98° C. The aqueous pot residue was cooled to 10°–15° C. and filtered to give substantially pure crystalline product, assayed at 126 g. of 3-amino-4-ethoxyacetanilide, 65–70% of theory, based on the 2,4-dinitrochlorobenzene starting material.

As in the above Examples, the following compounds were or could be made:

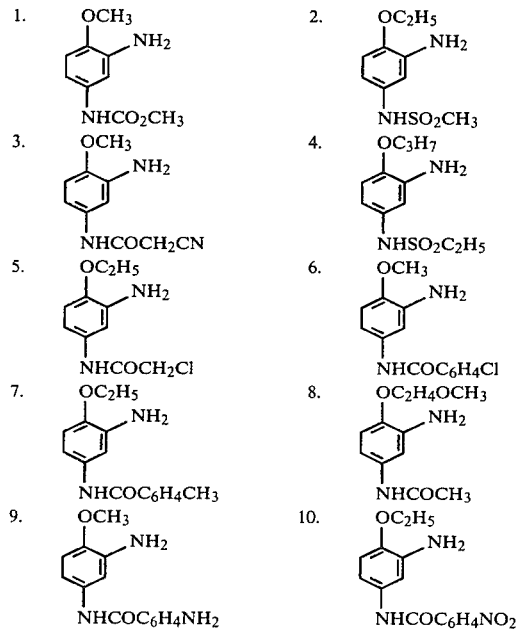

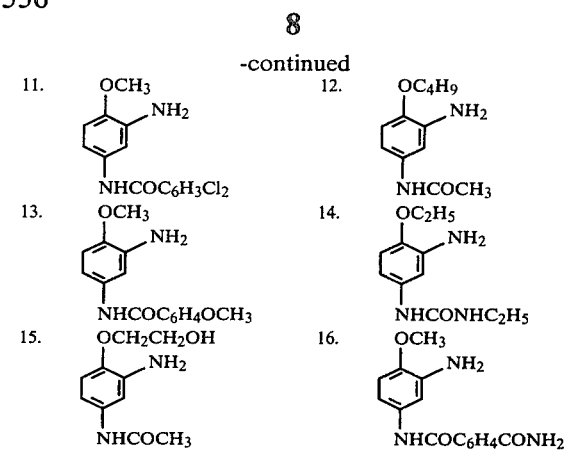

The acylanilides produced by the process of this invention are useful as coupler intermediates in the synthesis of useful azo-dyes. For instance the navy blue dye of structure XXI may be synthesized from compound I, as taught in U.S. Pat. No. 3,533,722, according to the following reaction sequence:

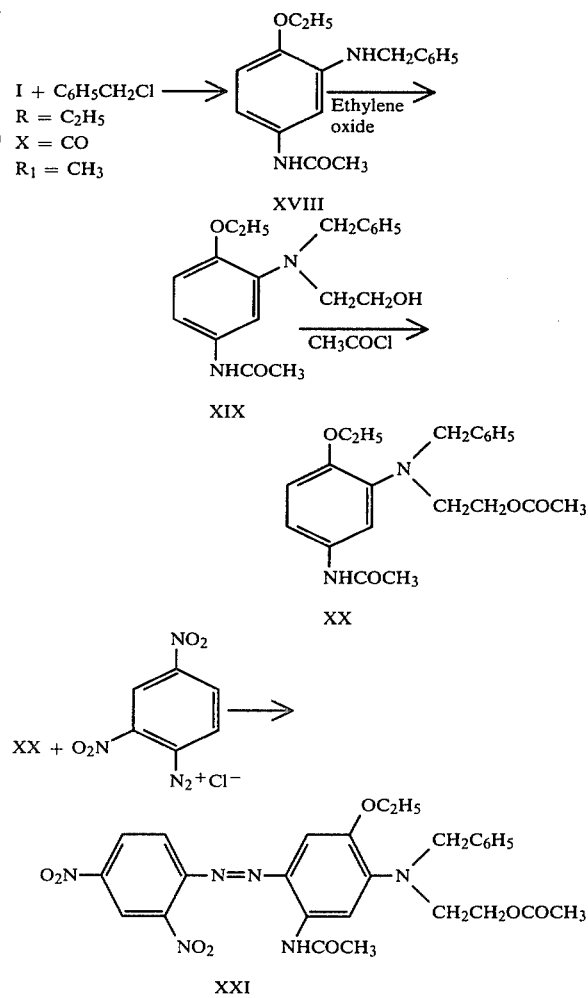

The above reaction sequence can also be carried out on I, where X and $R_1$ are as above, and R is $HOCH_2CH_2$—, to give the analog of dyestuff XXI, where the 3-ethoxy group is replaced by the hydroxyethoxy group. The required coupler intermediate I for this preparation is obtained by the process of Example 1, substituting ethylene glycol for the methanol used therein.

Other couplers which are readily made from an acylanilide of this invention include

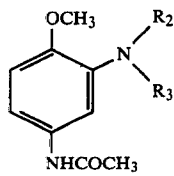

XXII R₂ = —CH₂CH₂CN; R₃ = —CH₂CH₃
XXIII R₂ = R₃ = —CH₂CH₂OCOCH₃

Particularly useful navy dyes are obtained by coupling XXII and XXIII with diazotized 2,4-dinitro-6-bromoaniline. Coupler XXII is obtained by sequential alkylation of 3-amino-4-methoxyacetanilide, first with one equivalent of acrylonitrile and then one equivalent of diethylsulfate. Coupler XXIII is obtained by alkylation of 3-amino-4-methoxyacetanilide with two equivalents of ethylene oxide, followed by esterification with two equivalents of acetic anhydride.

I claim:

1. A process for the manufacture of an acylanilide compound of the structure

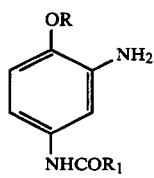

where R is hydrogen, lower alkyl, hydroxy-lower alkyl or lower alkoxy-lower alkyl; and $R_1$ is lower alkyl, phenol, lower alkylphenyl, lower alkoxy, lower alkoxyphenyl, chlorophenyl, nitrophenyl, dichlorophenyl, chloro-lower alkyl, cyano-lower alkyl, lower alkyl amino, sulfamoylphenyl, carbamoylphenyl or lower alkoxy-lower alkyl;

comprising the step of treating an alcohol solution of a diamino compound of the structure

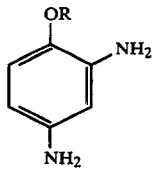

with a substantially equivalent weight of an acylating agent of structure $R_1COOCOR_1$, added over a period of at least about 1 hour at a temperature in the range of about 0° to about 5° C., to give an alcohol solution of the acylanilide compound.

2. The process of claim 1, wherein R and $R_1$ are independently methyl, ethyl, n-propyl, or n-butyl, and the alcohol is ROH.

3. The process of claim 2, wherein R and $R_1$ are each independently methyl or ethyl.

4. The process of claim 1, further comprising a first step of subjecting an alcohol suspension of a dinitro compound of the structure

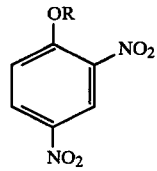

to reducing conditions to give an alcohol solution of the diamino compound for the subsequent treatment with the acylating agent, without isolation of the diamino compound from the alcohol solution.

5. The process of claim 4, wherein R is lower alkyl, hydroxy-lower alkyl or lower alkoxy-lower alkyl.

6. The process of claim 5, wherein the reducing conditions include hydrogen gas under super-atmospheric pressure, in the presence of a noble metal catalyst, and stirring.

7. The process of claim 6, wherein R and $R_1$ are each independently methyl or ethyl, and the alcohol is ROH.

8. The process of claim 4, wherein the reducing conditions include iron in aqueous or alcoholic suspension at a pH in the range of 3-6.5.

9. The process of claim 4, wherein R is not hydrogen, and wherein the dinitro compound is provided, in alcoholic suspension, by treating 2,4-dinitrochlorobenzene, in an alcohol of structure ROH, with alkali.

10. A process for the manufacture of an acylanilide of the structure

where R and $R_1$ are each independently methyl or ethyl, comprising the steps of (1) providing a suspension of 2,4-dinitro-chlorobenzene in an alcohol of structure ROH, and (2) sequentially treating the alcoholic suspension with alkali, hydrogen gas in the presence of a noble metal catalyst, and a substantially equivalent weight of an acylating agent of structure $R_1COO-COR_1$, added over a period of at least about 1 hour at a temperature in the range of about 0° to about 5° C., whereby the 2,4-dinitrochlorobenzene is converted to the acylanilide.

11. The process of claim 10, wherein the 2,4-dinitrochlorobenzene is converted to the acylanilide without isolation or purification of the intermediates.

12. The process of claim 11, wherein the hydrogen gas is at a pressure of about 40-80 psig and the noble metal catalyst is a palladium on carbon catalyst.

* * * * *

UNITED STATES PATENT AND TRADEMARK OFFICE
CERTIFICATE OF CORRECTION

PATENT NO. : 4,283,556
DATED : AUGUST 11, 1981
INVENTOR(S) : PHILIP C. LANG

It is certified that error appears in the above—identified patent and that said Letters Patent is hereby corrected as shown below:

CLAIM 1, COLUMN 9, LINE 44 reads:

"$R_1$ is lower alkyl, phenol, lower alkylphenyl, lower"

Should read:

-- $R_1$ is lower alkyl, phenyl, lower alkylphenyl, lower --

Signed and Sealed this

Fifth Day of January 1982

[SEAL]

Attest:

Attesting Officer

GERALD J. MOSSINGHOFF

Commissioner of Patents and Trademarks